United States Patent [19]

Ogawa

[11] 4,286,585
[45] Sep. 1, 1981

[54] BEND ANGLE CONTROL FOR ENDOSCOPE

[75] Inventor: Mototuga Ogawa, Chofu, Japan

[73] Assignee: Olympus Optical Co., Ltd., Tokyo, Japan

[21] Appl. No.: 101,077

[22] Filed: Dec. 7, 1979

[30] Foreign Application Priority Data

Dec. 22, 1978 [JP] Japan .................. 53-158870

[51] Int. Cl.³ .............................................. A61B 1/06
[52] U.S. Cl. ........................... 128/6; 128/772;
128/657; 128/DIG. 9; 254/134.3 FT; 250/227; 356/241
[58] Field of Search ........................ 128/3–8, 128/DIG. 9, 772, 657; 350/96.26; 254/134.3 FT; 250/358 P, 227; 15/104.3 SN; 33/302; 73/623, 634; 356/241

[56] References Cited

U.S. PATENT DOCUMENTS

| 3,744,906 | 7/1973 | Sato et al. ............... | 128/6 |
| 4,054,128 | 10/1977 | Seufert et al. ............. | 128/DIG. 9 |
| 4,199,258 | 4/1980 | Dau ........................ | 356/241 |

FOREIGN PATENT DOCUMENTS

| 2504663 | 8/1976 | Fed. Rep. of Germany ........ | 128/4 |
| 5025083 | 3/1975 | Japan ...................... | 128/4 |
| 5342481 | 4/1978 | Japan ...................... | 128/4 |

Primary Examiner—Robert W. Michell
Assistant Examiner—Arthur S. Rose

[57] ABSTRACT

An endoscope which comprises a distal end portion containing an observation optical system, a flexible tube, a freely bendable section for connecting the distal end portion to the flexible tube and an optical transmission means for conducting an image picked up by the observation optical system to an eyepiece section.

The endoscope further comprises a plurality of photoelectric conversion elements spacially mounted on the surface of the optical transmission means which faces the eyepiece section, a bend angle control device for controlling the angle through which the freely bendable section is to be bent in accordance with data obtained from the photoelectric conversion elements in order to direct the tip of the distal end portion to the substantial center of the cross section of, for example, the large intestine to be examined, and whereby, when the endoscope is inserted into the large intestine, the bend angle control device automatically directs the tip of the distal end portion to the substantial center of the cross section of the large intestine in order to prevent said tip of the distal end portion to be forcefully pressed against the inner wall of the large intestine.

5 Claims, 23 Drawing Figures

BEND ANGLE CONTROL FOR ENDOSCOPE

BACKGROUND OF THE INVENTION

This invention relates to an endoscope inserted into an intricately twisted coeliac tube.

Difficulties are often encountered in manually inserting an endoscope into the digestive tract of a living body to effect, for example, medical examination. The difficulties chiefly arise from the intricately twisted form of the digestive tract, for example, the large intestine. Therefore, it has hitherto been necessary to try to frequently control the direction in which the distal end portion of an endoscope, for example, a colon scope is inserted into the colon in conforming to the intricately twisted form of the colon in order to effect the smooth full insertion of said instrument. However, the above-mentioned control sometimes caused the distal end portion of the endoscope to forcefully press the inner wall of the colon, thus imparting great pain to a patient, and unavoidably prolonging the time of examination.

SUMMARY OF THE INVENTION

This invention has been accomplished in view of the above-mentioned circumstances and is intended to provide an endoscope, whose distal end portion is automatically so controlled as to be always directed to the substantial center of the cross section of a coeliac tube.

To this end, the present invention provides an endoscope which comprises:
  a distal end portion containing an observation optical system;
  a flexible tube;
  a freely bendable section for connecting the distal end portion to the flexible tube;
  an optical transmission device for conducting an image picked up by the observation optical system to the eyepiece side of the endoscope;
  a plurality of photoelectric conversion elements specially arranged on the eyepiece side of the endoscope; and
  a bend angle control device for controlling the angle through which the freely bendable section is to be bent in accordance with data delivered from the plural photoelectric conversion elements in order to direct the distal end portion of the endoscope to the substantial center of the cross section of, for example, a coeliac tube to be examined.

With the endoscope of this invention arranged as described above, the tip of the distal end portion, when inserted into a coeliac tube, is automatically directed to the substantial center of the coeliac tube in order to be prevented from forcefully pressing the inner wall of the coeliac tube. Even where, therefore, the distal end portion of the endoscope is carelessly inserted into, for example, the large intestine of a patient, he is little likely to suffer an unpleasant feeling or pain.

DESCRIPTION OF THE PREFERRED EMBODIMENTS

There will now be described by reference to the accompanying drawing an endoscope embodying this invention. For briefness of description, the same or similar parts are denoted by the same or similar reference numerals.

Figure 1:
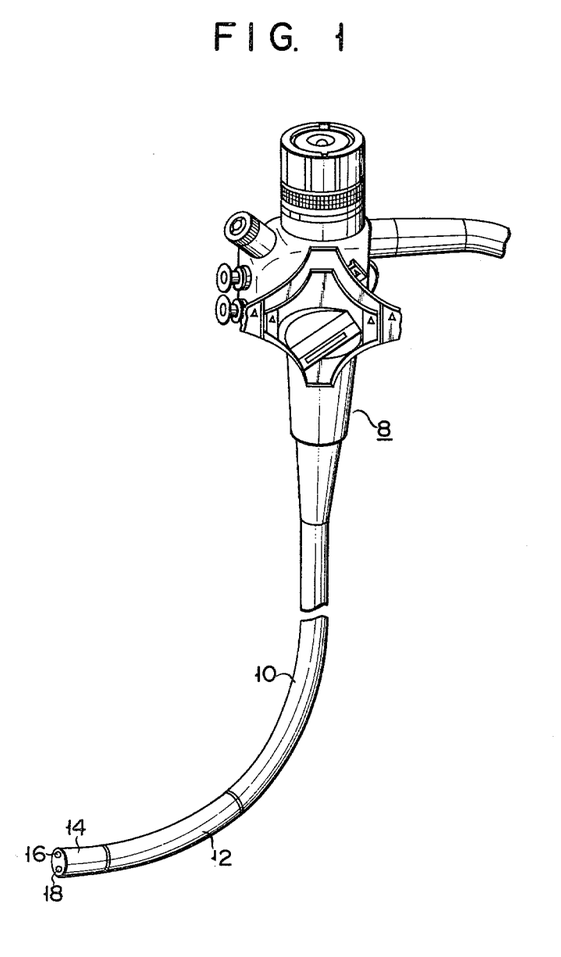
FIG. 1 is an oblique external view of an endoscope to which this invention is applied.
Figures 2, 3, 4:
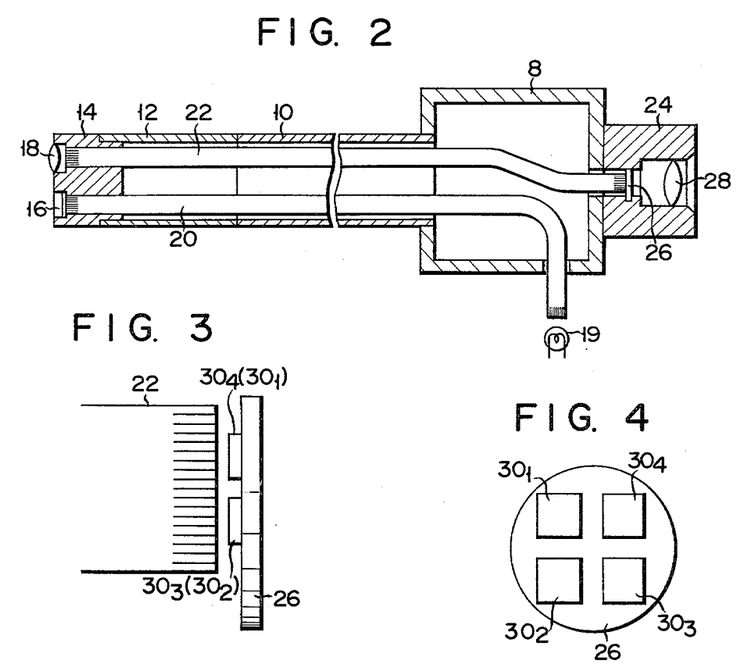
FIG. 2 is a longitudinal sectional view of an endoscope embodying this invention, showing the internal arrangement thereof.
FIG. 3 is an enlarged view of that section of FIG. 2 in which an optical fiber 22 and a photoelectric conversion element support 26 are set.
FIG. 4 shows the arrangement of photoelectric conversion elements 30 mounted on said support 26.

Referring to FIG. 1 showing the external appearance of an endoscope embodying this invention, a flexible tube (insertion tube) 10 connected to an operation section 8 is coupled to a distal end portion 14 throught a freely bendable section 12. The tip of the distal end portion 14 is fitted with a light guide 16 and an object lens 18 included in an observation optical system. All the above-mentioned members may be formed in the same manner as those used with the conventional endoscope. The distal end portion 14 is inserted into, for example, the large instestine of a patient. FIG. 2 is a longitudinal sectional view of the endoscope of FIG. 1, showing its internal arrangement. A light guide 16 is connected to a light source 19 through a light fiber 20. The object lens 18 is connected to an eyepiece section 24 through an image guide fiber 22. Set in the eyepiece section 24 is a photoelectric conversion element support 26 which faces the end face of the image guide fiber 22. An eyepiece 28 is mounted on an axis perpendicular to the surface of the support 26. At the time of observation, the support 26 is removed from the end face of the image guide fiber 22.

FIG. 3 is an enlarged view of that section of the endoscope in which the end face of the image guide fiber 22 and photoelectric conversion element support 26 are set to face each other.

Figure 4A:
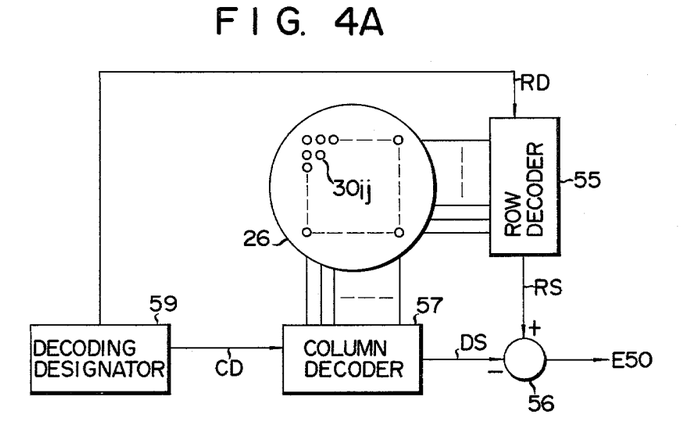
FIG. 4A illustrates the matrix arrangement of photoelectric conversion elements 30.

Photoelectric conversion elements $30_1$, $30_2$, $30_3$, $30_4$ are mounted on that surface of their support 26 which is set opposite to the end face of the image guide fiber 22. The photoelectric conversion element may be formed of, for example, a cadmium sulfide cell, solar cell or phototransistor. The photoelectric conversion elements $30_1$ to $30_4$ are arranged on their support 26, as illustrated in FIG. 4. In the foregoing embodiment, four photoelectric conversion elements $30_1$ to $30_4$ are provided. However, it is possible to apply a for larger number of photoelectric conversion elements in the matrix form as illustrated in FIG. 4A. The row units of the matrix-arranged photoelectric conversion elements $30_{ij}$ are connected to a row decoder 55. The column units thereof are connected to a column decoder 57. The decoders 55, 57 are respectively supplied with the prescribed code data RD, CD delivered from a decoding designator 59 which includes a clock generator. Upon receipt of the data CD, RD, the decoders 55, 57 respectively send forth signals RS, DS corresponding to the prescribed combinations of the photoelectric conversion elements $30_{ij}$. The signals RS, DS are conducted to a difference detector 56, which in turn produces a signal E50 denoting a difference between the signals RS, DS. Now let it be assumed that the photoelectric conversion elements $30_{ij}$ are arranged in the matrix form of $3\times3$, and that the data RD, CD respectively specify the photoelectric conversion elements $30_{11}$, $30_{33}$. Then the difference signal E50 denotes a difference between a photoelectric output signal from the photoelectric conversion element $30_{11}$ and a photoelectric output signal from the photoelectric conversion element $30_{33}$. At this time, the bend angle control of the freely bendable section 12 is carried out on a line extended between the photoelectric conversion elements $30_{11}$, $30_{33}$. The matrix-arranged photoelectric conversion elements $30_{ij}$ may be combined by the decoding designator 59 in accordance with various factors such as the type of a coeliac tube to be examined and other conditions. It is possible to change the size of the photoelectric conversion elements $30_{ij}$ and their arranged form.

Figure 5:
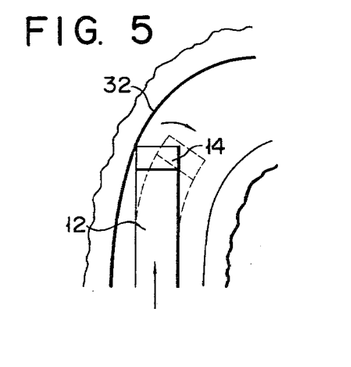
FIG. 5 indicates the manner in which the proximity of the distal end portion 14 of the endoscope of FIG. 2 is bent (as shown in broken lines) when said endoscope is inserted into, for example, the intricately twisted large intestine.

FIG. 5 illustrates the manner in which the endoscope of FIG. 2 is bent when inserted into, for example, the large intestine 32. An illumination light is issued from the light guide 16 set at the tip of the distal end portion 14 of the endoscope. The illumination light reflected from the inner wall of the large intestine 32 is returned to the object lens 18. The image of the inner wall of the large intestine 32 brought into the object lens 18 is transmitted to the photoelectric conversion elements $30_1$ to $30_4$ through the image guide fiber 22. It is to be noted that the intensity of a reflection is inversely proportional to a distance between the point on the inner wall of the large intestine 32 from which the reflection starts and the point on the end face of the distal end portion 14 or which said reflection falls. In other words, a reflection brought to the left side of the end face of the distal end portion 14 has a greater intensity than a reflection falling on the right side of the end face of the distal end portion 14.

Figure 6:
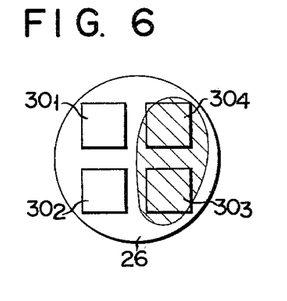
FIG. 6 indicates the distribution of brightness on the photoelectric conversion element support 26 when the endoscope is inserted into the large intestine as shown in FIG. 5.

FIG. 6 illustrates the distribution of brightness on the photoelectric conversion element support 26, when the endoscope is inserted, for example, into the large intestine 32. Since a reflection falling on the right side of the end face of the distal end portion 14 is weak, the right side of the support 26 becomes dark as illustrated in hatching. In other words, a group of signals drawn out from the left side photoelectric conversion elements $30_1$, $30_2$ has a different level from a group of signals issued from the right side photoelectric conversion elements $30_3$, $30_4$. Where the angle through which the freely bendable section 12 is to be bent is so controlled as to reduce the above-mentioned difference between the electric signals to the minimum, then the distal end portion 14 of FIG. 5 is turned in a direction indicated in broken lines. Then, the central portion of the surface of the photoelectric conversion element support 26 becomes dark, whereas the proximity of said control portion is uniformly rendered bright. As a result, the automatic bend angle control system attains the intended target. Later when a pushing force is applied to the endoscope in the direction of an arrow indicated in FIG. 5, then the endoscope is smoothly inserted into the large intestine, without causing the tip of the distal end portion 14 to be caught by the inner wall of the intricately twisted large intestine 32.

Figure 7:
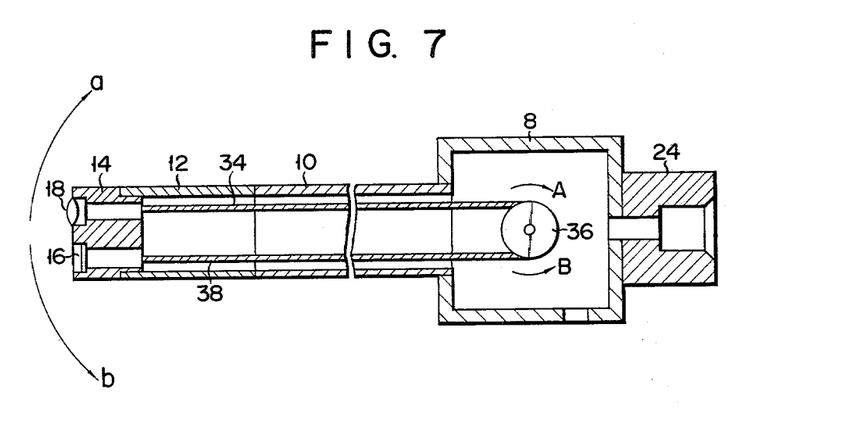
FIG. 7 shows the arrangement of a bend angle control device fitted to the endoscope of FIG. 2.
Figure 8:
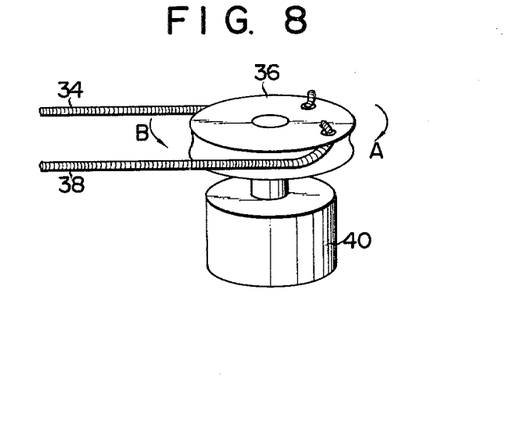
FIG. 8 is an oblique view showing the manner in which a pulley 36 of endoscope-bending wires 34, 38 shown in FIG. 7 is coupled to a servo motor 40.

FIG. 7 shows the internal arrangement of a device for controlling the angle through which the freely bendable section 12 is to be bent. For better understanding, the light fiber 20 and image guide fiber 22 are emitted from the endoscope shown in FIG. 7. The inner end of the peripheral wall on one side of the distal end portion 14 is connected to one side of the pulley 36 of endoscope-bending wires 34, 38 by means of the wire 34. The inner end of the peripheral wall in the other side of the distal end portion 14 is connected to the other side of said pulley 36. The wire pulley 36 is fitted, as shown in FIG. 8, to the shaft of the servo motor 40. When the servo motor 40 is rotate in the direction of the arrow A of FIG. 8, then the distal end portion 14 is bent in the direction of the arrow a of FIG. 7. Conversely where the servo motor 40 is driven in the direction of the arrow B of FIG. 8, then the distal end portion 14 is bent in the direction of the arrow b of FIG. 7. In other words, the distal end portion 14 is bent in accordance with the direction in which the servo motor 40 is rotated and the angle through which said rotation is made. The servo motor 40 may be formed of not only the electric type, but also the pulse or oil pressure type. The force of changing the bend angle of the distal end portion 14 may be transmitted by means of a fluid (for example, oil pressure) instead of the endoscope-bending wires 34, 38. FIG. 7 shows the arrangement of a bend angle control device set in a direction parallel to the drawing surface. Actually, however, another bend angle control device is provided which extends in a direction perpendicular to the drawing surface. A combination of these two bend angle control devices can bend the freely bendable section 12 in any desired direction. The bend angle control device may be devised in various modifications. It is possible to utilize the bend angle control device set forth in the U.S. Pat. No. 4,054,128.

Figure 9:
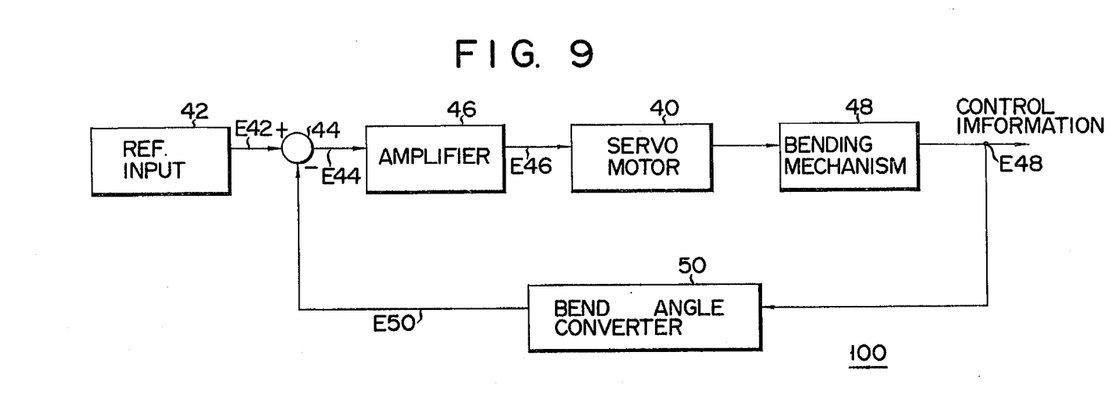
FIG. 9 is a block circuit diagram of a bend angle control device of FIG. 7.

FIG. 9 is a block circuit diagram of the bend angle control device 100 of FIG. 7. A reference signal E42 delivered from a reference input generator 42 is supplied to a difference detector 44. The reference signal E42 is generally chosen to have a zero or prescribed potential. An output difference signal E44 from the difference detector 44 is conducted to an amplifier 46, which in turn supplies the servo motor 40 with a drive signal E46 produced by amplifying the difference signal E44. The servo motor 40 mechanically drives the bending mechanism 48 in accordance with the magnitude of the drive signal E46 and its polarity (or phase). The bending mechanism 48 is formed of the members 10, 12, 14, 34, 36, 38 shown in FIGS. 2, 3 and 7. A bend angle control signal E48 denoting the angle through which the distal end portion 14 is transmitted to the bend angle converter 50. The bend angle converter 50 supplies the difference detector 44 with a comparison signal E50 corresponding to the bend angle control signal E48. The difference detector 44 substracts the comparison signal E50 from the reference signal E42. In other words, the difference signal E44 denotes a difference between the reference signal E42 and the comparison signal E50. FIG. 9 is a block circuit diagram of a servo mechanism which is supplied with a steady-state deviation in accordand with the reference signal E42. Where, therefore, the reference signal E42 is manually changed, then the bend angle of the freely bendable section 12 can be manually varied.

Figure 10:
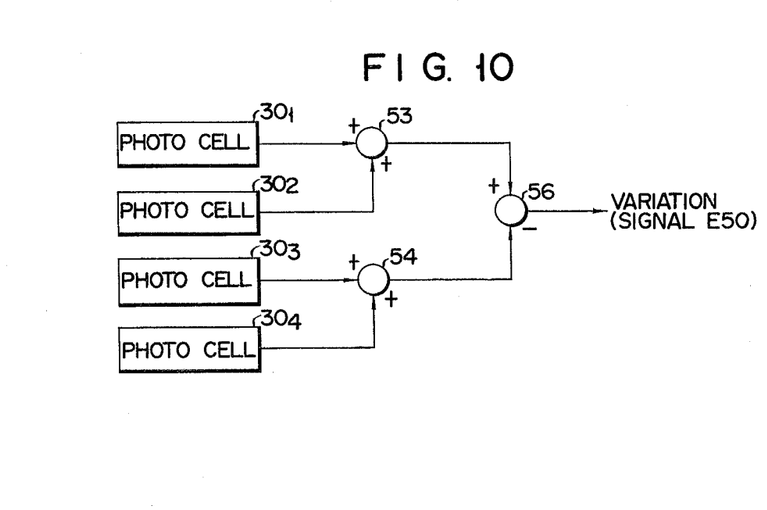
FIG. 10 indicates the arrangement of the process by which a signal E50 given in FIG. 9 is composed.
Figure 11:
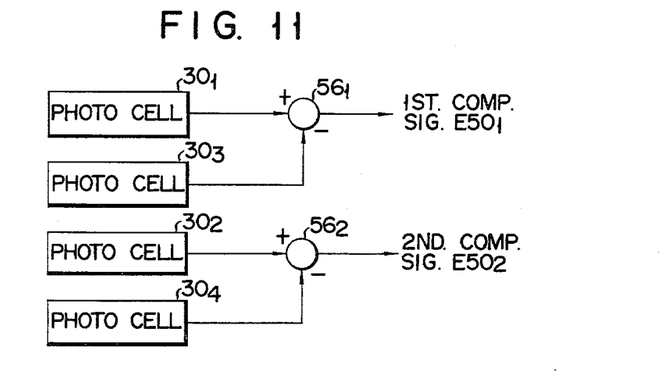
FIG. 11 shows the arrangement of a modification of the process of FIG. 10 in which two different signals $E50_1$, $E50_2$ are composed to carry out a 2-dimensional bend angle control.

FIG. 10 shows the process by which the signal E50 is composed. The process is included in the bend angle converter 50 of FIG. 9. Output signals from the photoelectric conversion elements $30_1$, $30_2$ are added together in an adder 53. Output signals from the photoelectric conversion elements $30_3$, $30_4$ are added together in an adder 54. Output signals from the adders 53, 54 are processed by subtraction in the variation detector 56. The variation detector 56 sends forth the comparison signal E50. FIG. 10 shows the arrangement of a process by which a 2-dimensional bend angle control is carried out. Where a 3-dimensional bend angle control is to be carried out, the following steps should advisably be taken. Namely as shown in FIG. 11, a first comparison signal $E50_1$ is composed of output signals from the photoelectric conversion elements $30_1$, $30_3$. A second comparison signal $E50_2$ is composed of output signals from the photoelectric conversion elements $30_2$, $30_4$. Two servo devices are provided whose arrangements are shown in FIGS. 7 to 9. One of the two servo devices is supplied with the first comparison signal, and the other with the second comparison signal.

Figure 12:
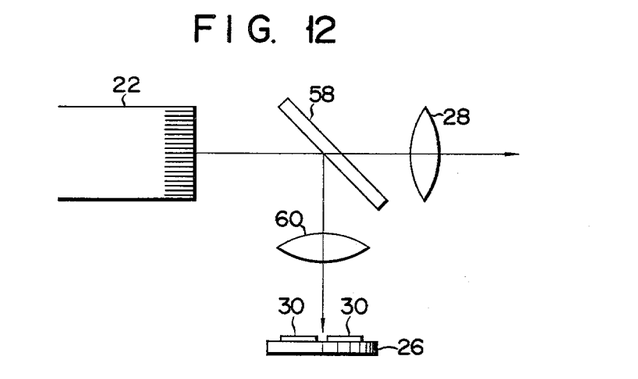
FIG. 12 illustrates an optical system for transmitting optical data for bend angle control to the photoelectric conversion elements 30.

FIG. 12 shows the arrangement of an optical system for transmitting optical data on the required bend angle control to the photoelectric conversion element 30. An endoscope arranged as shown in FIG. 2 has the drawback that while the angle through which the freely bendable section 12 is automatically controlled, it is impossible to observe the interior condition of a coeliac tube. The reason for this is that the photoelectric conversion element support 26 obstructs that portion of a light path which extends between the proximal end of the image guide fiber 22 and the eyepiece section (lens) 28. In contrast, where the optical system of FIG. 12 is applied to the endoscope arranged as shown in FIG. 2, then it is possible to carry out the observation of the interior condition of a coeliac tube with the automatic control of the angle through which the distal end portion 14 of the endoscope is to be changed. In other words, optical data delivered from the image guide fiber 22 is branched and transmitted to the eyepiece section 28 through a half mirror 58. At this time, part of the optical data is reflected from the half-mirror 58. The reflection is also conducted to the support 26 of the photoelectric conversion elements 30 through a lens 60.

Figure 13:
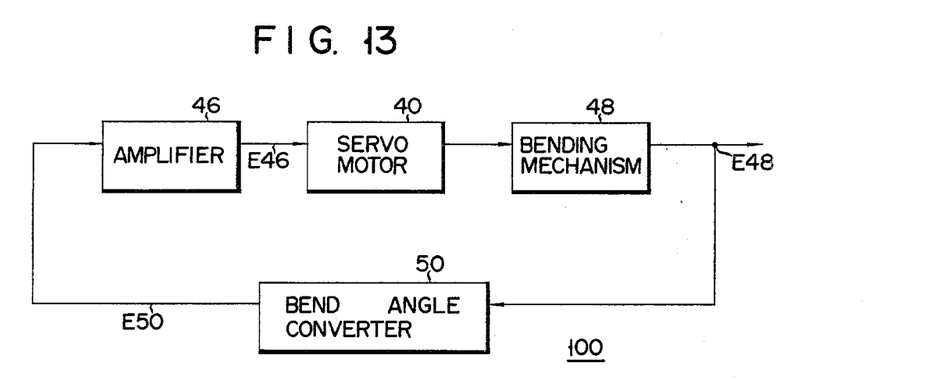
FIGS. 13 and 14 are the block circuit diagrams of the modifications of the bend angle control device of FIG. 9.

FIG. 13 is a block circuit diagram of a modification of the bend angle control device 100 of FIG. 9. The reference input generator 42 and difference detector 44 are omitted from FIG. 13. With the servo device of FIG. 13, the angle through which the freely bendable section 12 is to be bent is not manually controlled. However, the servo device of FIG. 13 can so control the above-mentioned bend angle of the freely bendable section 12 as to automatically prevent the tip of the distal end portion 14 from being pressed against the inner wall of a coeliac tube, for example, the large intestine.

Figure 14:
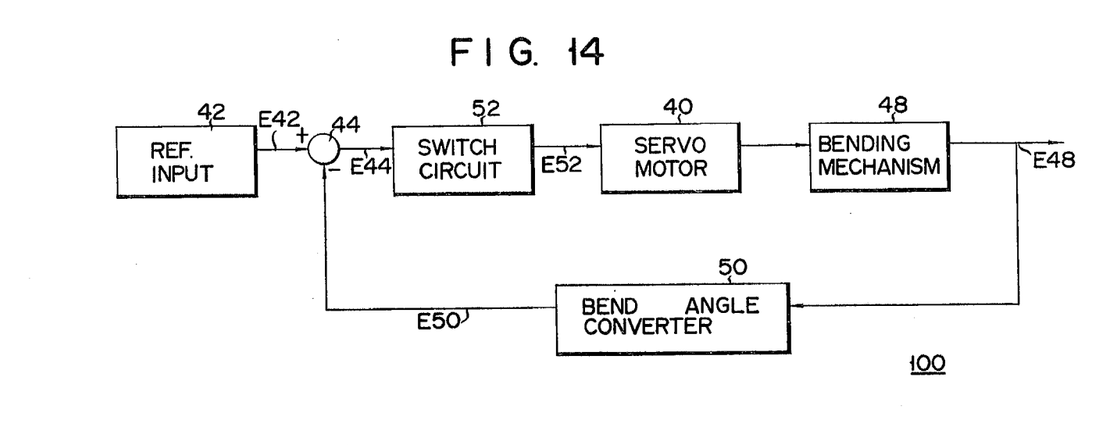

FIG. 14 is a block circuit diagram of another modification of the bend angle control device 100 of FIG. 9. The construction of FIG. 9 continuously controls the angle through which the freely bendable section 12 is to be bent. In contrast, the modification of FIG. 14 carries out the above-mentioned bend angle control by a different process described below. Namely, the difference signal E44 drawn out from the difference detector 44 is supplied to a switch circuit (comparator circuit) 52 the switch circuit 52 sends forth a drive signal E52 to the servo motor 40. Though having a fixed amplitude, the drive signal E52 is rendered positive or negative in accordance with the difference signal E44. Now let it be assumed that where the tip of the distal end portion 14 of the endoscope is pressed against the inner wall of the large intestine 32, there results $E42-E50<0$. At this time the difference signal E44 is rendered negative. As a result, the switch circuit 52 supplies a negative drive signal E52 to the servo motor 40. Accordingly, the servo motor 40 is driven backward to decrease a value represented by the comparison signal E50. The reverse run of the servo motor 40 leads to $E42-E50>0$. As a result, the difference signal E44 is rendered positive, causing the switch circuit 52 to deliver a positive drive signal E52+ to the servo motor 40. Thus, the servo motor 40 makes a normal run to increase a value represented by the comparison signal E50. Where the normal run of the servo motor 40 results in $E42-E50<0$, then the aforesaid bend angle control is repeated. Eventually, the repeated changeover operation of the switch circuit 52 automatically so controls the difference $|E42-E50|$ as to reduce said difference to zero on the average. Therefore the modification of the servo device arranged as shown in FIG. 14 can control the angle through which the freely bendable section 12 is to be bent is substantially the same manner as the servo device of FIG. 9.

Figure 15:
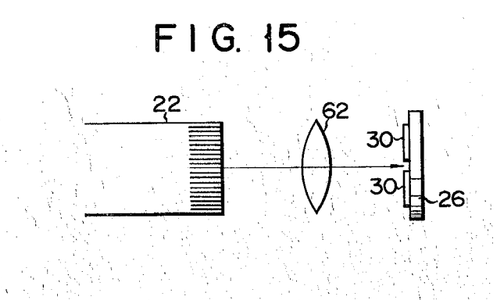
FIGS. 15 to 22 show the arrangements of the modifications of the optical system of FIG. 12.
Figure 16:
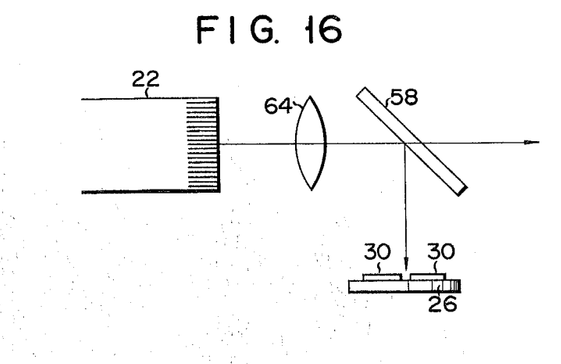
Figure 17:
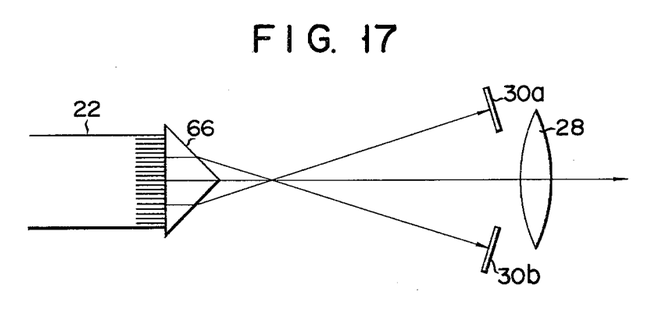
Figure 18:
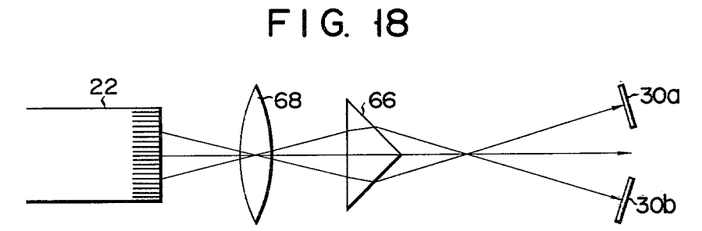

FIGS. 15 to 22 illustrate the modifications of the optical system of FIG. 12. In FIG. 15, optical data issued from the proximal end of the image guide fiber 22 is conducted straightway to the photoelectric conversion elements 30 through a lens 62. In FIG. 16, optical data which has passed through a lens 64 and is reflected from the half-mirror 58 is carried to the photoelectric conversion elements 30. In FIG. 17, optical data sent forth from the image guide fiber 22 is divided in two parts by a prism 66. Optical data conducted through the upper half portion of the prism 66 is transmitted to a photoelectric conversion element 30b. Optical data carried through the lower half portion of the image guide fiber 22 is delivered to a photoelectric conversion element 30a. In FIG. 18, optical data passing through the image guide fiber 22 is transmitted to the prism 66 through a lens 68. The prism 66 is made movable and is removed from a light path at the time of observation.

Figure 19:
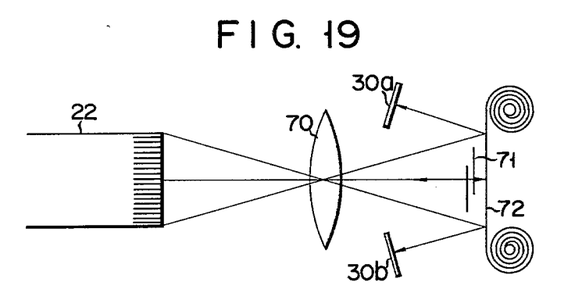

In FIG. 19, shows an arrangement by which optical data drawn out from the image guide fiber 22 is photographed. A light delivered from the image guide fiber 22 is conducted to the surface of the photographic film 72 through a photographic lens 70. Beams of a light reflected from the surface of a film 72 are divided into upper and lower portions with the axis of the image guide fiber 22 taken as the border line. The divided light beams are conducted to photoelectric conversion elements 30a, 30b respectively. The optical image to be photographed is carried to the sensitized surface of the film 72 through a shutter 71.

Figure 20:
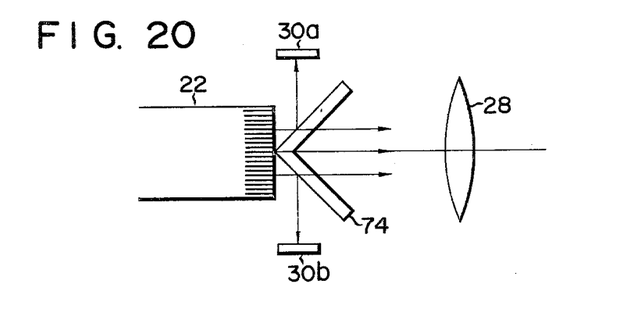

In FIG. 20, the end face of the image guide fiber 22 is fitted with an angularly bent half-mirror 74, both arms of which are symmetrically set with respect to the shaft of the image guide fiber 22. Optical data travelling through the upper half portion of the image guide fiber 22 is reflected from one arm of the half-mirror 74 to the photoelectric conversion element 30a. Optical data running through the lower half portion of the image guide fiber 22 is reflected from the other arm of the half-mirror 74 to the photoelectric conversion element 30b.

Figure 21:
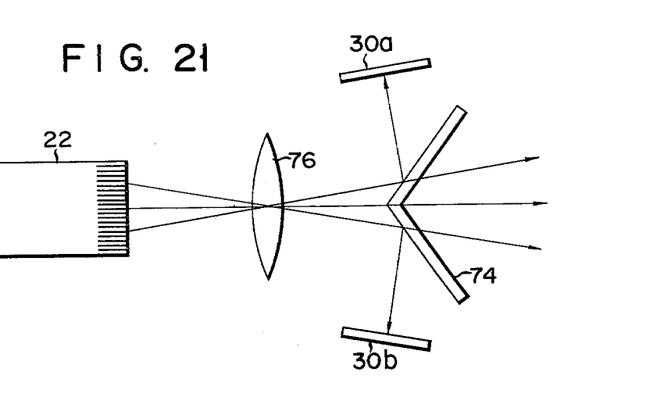

In FIG. 21, optical data drawn out from the image guide fiber 22 is carried to the angularly bent half-mirror 74 through a lens 76.

Figure 22:
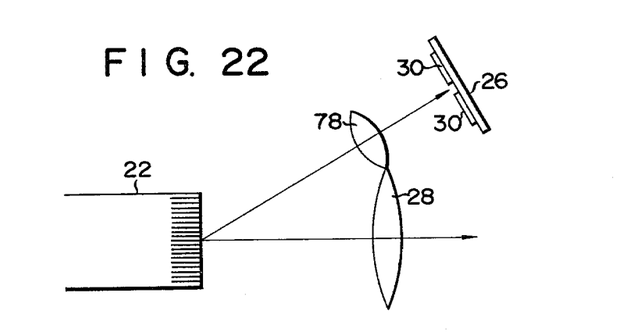

In FIG. 22, optical data obliquently sent forth from the end face of the image guide fiber 22 is delivered to the photoelectric conversion elements 30 through a lens 78.

With the endoscope of this invention, the angle through which the distal end portion 14 is to be bent is automatically so controlled as to prevent the tip of said distal end portion 14 from forcefully pressing the inner wall of a coeliac tube. In other words, the direction in which the tip of the distal end portion 14 is bent is automatically changed in accordance with the distorted form of a coeliac tube. Therefore, the endoscope of this invention can be smoothly inserted into an intricately twisted coeliac tube such as the large intestine simply by push when observation is made of the interior condition of the large intestine. Consequently, an operator unskilled in the handling of an endoscope can easily insert the endoscope into a coeliac tube. Since the tip of the distal end portion 14 is not forcefully pressed against the inner wall of the coeliac tube, an examinee or patient suffers little pain. The deep region of the coeliac tube can be touched by the smoothly inserted endoscope in a short time.

Although specific constructions have been illustrated and described herein, it is not intended that the invention be limited to the elements and constructions disclosed. One skilled in the art will recognize that the particular elements or subconstructions may be used without departing from the scope and spirit of the invention.

What is claimed is:
1. An endoscope which comprises:
   (a) a distal end portion containing an observation optical system;
   (b) a flexible tube;
   (c) a freely bendable section for connecting the distal end portion to the flexible tube;
   (d) an optical transmission means for conducting an image picked up by the observation optical system to the eyepiece section of the endoscope;
   (e) a plurality of photoelectric conversion means spacially arranged on the eyepiece section side to detect the distribution of the brightness of an image picked up by the observation optical system; and
   (f) a bend angle control means for controlling the angle through which the freely bendable section is to be bent in accordance with data delivered from the photoelectric conversion means in order to direct the distal end portion to the substantial center of a coeliac tube to be examined.

2. The endoscope according to claim 1, wherein the bend angle control means includes:
   a reference input generator means;
   a difference detector means for detecting a difference between a reference signal produces from the reference input generator means and a comparison signal corresponding to the data sent forth from the photoelectric conversion means;
   an amplifier means for amplifying a difference signal delivered from the difference detector means; and
   a freely bendable section driving means actuated by a drive signal sent forth from the amplifier means, and whereby the bend angle control means constitutes a servo mechanism in which the angle through which the freely bendable section is to be bent is defined on the basis of the reference signal.

3. The endoscope according to claim 1, wherein the bend angle control means includes;
   a reference input generator means;
   a difference detector means for detecting a difference between a reference signal issued from the reference input generator means and a comparison signal corresponding to data obtained from the photoelectric conversion means;
   a switch means for producing a drive signal which is rendered positive or negative in accordance with the level of a difference signal delivered from the difference detector means; and
   a freely bendable section driving means actuated by a drive signal sent forth from the switch means, and whereby the bend angle control means constitutes a servo mechanism in which the angle through which the freely bendable section is to be bent is defined on the basis of the reference signal.

4. The endoscope according to claim 2 or 3, wherein the freely bendable section driving means includes a servo motor for controlling the angle through which said freely bendable section is to be bent.

5. The endoscope according to anyone of claims 1 to 3, which further comprises a light path branching means for unobstructedly conducting to the photoelectric conversion means an optical image which is to be transmitted to the eyepiece section when the bend angle control of the freely bendable section is carried out.

* * * * *